United States Patent [19]

Findeisen et al.

[11] Patent Number: 5,234,897

[45] Date of Patent: * Aug. 10, 1993

[54] HERBICIDAL 3-AMINO-5-AMINOCARBONYL-1,2,4-TRIAZOLES

[75] Inventors: Kurt Findeisen; Hans-Joachim Santel, both of Leverkusen; Klaus Lürssen; Robert R. Schmidt, both of Bergisch-Gladbach, all of Fed. Rep. of Germany

[73] Assignee: Bayer Aktiengesellschaft, Leverkusen, Fed. Rep. of Germany

[*] Notice: The portion of the term of this patent subsequent to Jun. 4, 2008 has been disclaimed.

[21] Appl. No.: 762,044

[22] Filed: Sep. 18, 1991

Related U.S. Application Data

[63] Continuation of Ser. No. 552,648, Jul. 16, 1990, abandoned, which is a continuation-in-part of Ser. No. 324,361, Mar. 15, 1989, Pat. No. 5,021,081.

[30] Foreign Application Priority Data

Aug. 8, 1989 [DE] Fed. Rep. of Germany ....... 3926119

[51] Int. Cl.$^5$ ................. A01N 43/653; C07D 249/14
[52] U.S. Cl. ................................... 504/273; 548/264.8
[58] Field of Search ................ 71/92; 548/264.8; 504/273

[56] References Cited

U.S. PATENT DOCUMENTS 5,021,081 6/1991 Findeisen et al. ............... 548/264.8

FOREIGN PATENT DOCUMENTS 0048555 3/1982 European Pat. Off. .
0332991 9/1989 European Pat. Off. .

OTHER PUBLICATIONS

Chemical Abstracts, vol. 85, Sep. 13, 1976, No. 11, Voronkov, M. G. et al, Basicity and protonation center of 5(3)-substituted-3(5)-amino-1,2,4-triazole p. 487, spalte 1.
Chemical abstracts, vol. 76, Mar. 13, 1972, No. 11 Nicholson, S. et al, Covalent hydrates as transient species in heterocyclic rearrangements, I. Ring fission of s-triazolo-pyrazines, p. 381 spalte 2.

*Primary Examiner*—Patricia L. Morris
*Attorney, Agent, or Firm*—Sprung, Horn, Kramer & Woods

[57] ABSTRACT

Herbicidal 3-amino-5-aminocarbonyl-1,2,4-triazoles of the formula $$R^1-NH-\underset{\underset{R^2}{|}}{C}\overset{N=N}{\underset{N}{\diagdown}}C-\underset{\underset{R^4}{|}}{\overset{O}{\underset{\|}{C}}}-N\overset{R^3}{\diagdown}$$

in which
R$^1$ and R$^2$ each independently is an alkyl or other organic radical, and
R$^3$ and R$^4$ each independently is hydrogen or an organic radical,
with the exception of the compounds in which
a) R$^1$=CH$_3$, R$^2$=CH$_3$, R$^3$=H, R$^4$=cyclohexyl;
b) R$^1$=CH$_3$, R$^2$=C$_2$H$_5$, R$^3$=H, R$^4$=CH$_2$-C(CH$_3$)$_3$;
c) R$^1$=CH$_3$, R$^2$=C$_2$H$_5$, R$^3$=H, R$^4$=1-phenyl-ethyl;
d) R$^1$=C$_2$H$_5$, R$^2$=CH$_3$, R$^3$=H, R$^4$=C(CH$_3$)$_3$;
e) R$^1$=CH$_3$, R$^2$=CH$_3$, R$^3$=CH$_3$, R$^4$=C(CH$_3$)$_3$;
f) R$^1$=CH$_3$, R$^2$=CH$_3$, R$^3$=H, R$^4$=—CH(CH$_3$)—CH=N—OCH$_3$ and
g) R$^1$=CH$_3$, R$^2$=CH$_3$, R$^3$=H, $$R^4 = \underset{CH_3}{\diagup}\hspace{-6pt}\bigcirc\hspace{-10pt}\diagdown H$$

15 Claims, No Drawings

HERBICIDAL 3-AMINO-5-AMINOCARBONYL-1,2,4-TRIAZOLES

This application is a continuation of application Ser. No. 552,648, filed Jul. 16, 1990 now abandoned, which is a continuation-in-part of application Ser. No. 324,361, filed Mar. 15, 1989, now U.S. Pat. No. 5,021,081.

The invention relates to new 3-amino-5-aminocarbonyl-1,2,4-triazole derivatives, to several processes for their preparation, and to their use as herbicides.

It is known that certain nitrogen-containing heterocycles (cf., for example, K. H. Büchel "Pflanzenschutz und Schädlingsbekämpfung" [Plant Protection and Pest Control] p. 170, Thieme Verlag Stuttgart 1977) have herbicidal properties.

Furthermore, certain substituted triazoles are the subject-matter of application Ser. No. 324,361, filed Mar. 15, 1989, now U.S. Pat. No. 5,021,081, corresponding to German Application P 3,809,053, filed Mar. 18, 1988.

However, the herbicidal activity of known compounds is not entirely satisfactory in all fields of application.

New 3-amino-5-aminocarbonyl-1,2,4-triazole derivatives of the general formula (I) have now been found

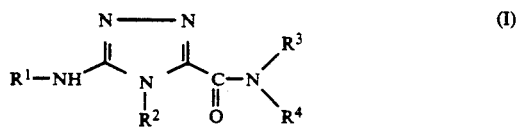

in which $R^1$ represents in each case straight-chain or branched alkyl having 1 to 8 carbon atoms, alkenyl having 2 to 8 carbon atoms, alkinyl having 2 to 8 carbon atoms, halogenoalkyl having 1 to 8 carbon atoms and 1 to 17 identical or different halogen atoms, halogenoalkenyl or halogenoalkinyl having in each case 2 to 8 carbon atoms and 1 to 15, or 13, identical or different halogen atoms, alkoxyalkyl having 1 to 6 carbon atoms in the individual alkyl moieties, or represents cycloalkyl having 3 to 7 carbon atoms, or represents cycloalkylalkyl having 3 to 7 carbon atoms in the cycloalkyl moiety and 1 to 6 carbon atoms in the straight-chain or branched alkyl moiety, or represents aralkyl which has 6 to 10 carbon atoms in the aryl moiety and 1 to 6 carbon atoms in the straight-chain or branched alkyl moiety and which is optionally monosubstituted or polysubstituted by identical or different substituents, or aryl which has 6 to 10 carbon atoms and which is optionally monosubstituted or polysubstituted by identical or different substituents, or heteroaryl which has 2 to 9 carbon atoms and 1 to 3 hetero atoms, in particular nitrogen, oxygen and/or sulphur, and which is optionally monosubstituted or polysubstituted by identical or different substituents, suitable substituents in each case being: halogen, cyano, nitro and in each case straight-chain or branched alkyl, alkoxy, alkylthio, halogenoalkyl, halogenoalkoxy or halogenoalkylthio, in each case having 1 to 4 carbon atoms and where appropriate 1 to 9 identical or different halogen atoms, $R^2$ represents in each case straight-chain or branched alkyl having 1 to 8 carbon atoms, alkenyl having 2 to 8 carbon atoms, alkinyl having 2 to 8 carbon atoms, halogenoalkyl having 1 to 8 carbon atoms and 1 to 17 identical or different halogen atoms, halogenoalkenyl having 2 to 8 carbon atoms and 1 to 15 identical or different halogen atoms, halogenoalkinyl having 2 to 8 carbon atoms and 1 to 13 identical or different halogen atoms, alkoxyalkyl having 1 to 6 carbon atoms in each of the individual alkyl moieties, or represents cycloalkylalkyl or cycloalkyl, in each case having 3 to 7 carbon atoms in the cycloalkyl moiety and where appropriate 1 to 6 carbon atoms in the straight-chain or branched alkyl moiety, or represents aralkyl or aryl, each of which has 6 to 10 carbon atoms in the aryl moiety and where appropriate 1 to 6 carbon atoms in the straight-chain or branched alkyl moiety and each of which is optionally monosubstituted or polysubstituted by identical or different substituents, suitable aryl substituents in each case being: halogen, cyano, nitro and in each case straight-chain or branched alkyl, alkoxy, alkylthio, halogenoalkyl, halogenoalkoxy or halogenoalkylthio, in each case having 1 to 4 carbon atoms and where appropriate 1 to 9 identical or different halogen atoms, and $R^3$ and $R^4$ independently of one another in each case represent hydrogen, or in each case represent straight-chain or branched alkyl having 1 to 18 carbon atoms, alkenyl having 2 to 8 carbon atoms, alkinyl having 2 to 8 carbon atoms, halogenoalkyl having 1 to 8 carbon atoms and 1 to 17 identical or different halogen atoms, halogenoalkenyl or halogenoalkinyl, in each case having 2 to 8 carbon atoms and 1 to 15, or 13, identical or different halogen atoms, cyanoalkyl having 1 to 8 carbon atoms, hydroxyalkyl having 1 to 8 carbon atoms and 1 to 6 hydroxyl groups, or alkoxyalkyl, alkoximinoalkyl, alkoxycarbonylalkyl or alkoxycarbonylalkenyl, in each case having up to 6 carbon atoms in the individual alkyl moieties, or alkenyl moieties, or alkylaminoalkyl or dialkylaminoalkyl, in each case having 1 to 6 carbon atoms in the individual alkyl moieties, or cycloalkyl, cycloalkylalkyl, cycloalkenyl or cycloalkenylalkyl, each of which has 3 to 8 carbon atoms in the cycloalkyl moiety, or cycloalkenyl moiety, and where appropriate 1 to 6 carbon atoms in the straight-chain or branched alkyl moiety and each of which is optionally monosubstituted or polysubstituted by identical or different substituents, suitable substituents in each case being: halogen, cyano and in each case straight-chain or branched alkyl or halogenoalkyl, in each case having 1 to 4 carbon atoms and where appropriate 1 to 9 identical or different halogen atoms, or in each case double-linked alkanediyl, or alkenediyl, in each case having up to 4 carbon atoms; $R^3$ and $R^4$ furthermore independently of one another represent heterocyclylalkyl which has 1 to 6 carbon atoms in the straight-chain or branched alkyl moiety and 1 to 9 carbon atoms as well as 1 to 3 hetero atoms—in particular nitrogen, oxygen and/or sulphur—in the heterocyclyl moiety and each of which is optionally monosubstituted or polysubstituted in the heterocyclyl moiety by identical or different substituents, suitable substituents being: halogen, cyano, nitro, and in each case straight-chain or branched alkyl, alkoxy, alkylthio, halogenoalkyl, halogenoalkoxy, halogenoalkylthio or alkoxycarbonyl, in each case having 1 to 5 carbon atoms and where appropriate 1 to 9 identical or different halogen atoms, and $R^3$ and $R^4$ furthermore independently of one another represent aralkyl, aroyl or aryl, each of which has 6 to 10 carbon atoms in the aryl moiety and where appropriate 1 to 8 carbon atoms in the straight-chain or branched alkyl moiety and each of which is optionally monosubstituted or polysubstituted by identical or different substituents, suitable aryl substituents in each case being: halogen, cyano, nitro, hydroxyl, in each case straight-chain or branched alkyl, alkoxy, alkylthio, halogenoalkyl, halogenoalkoxy, halogenoalkylthio, alkylsulphinyl, alkylsulphonyl, halogenoalkyl sulphinyl, halogenoalkylsulphonyl, alkanoyl or alkoxycarbonyl, in each case having 1 to 6 carbon atoms and where appropriate 1 to 9 identical or different halogen atoms, cycloalkyl having 3 to 6 carbon atoms or phenoxy, and suitable alkyl substituents which may be possible being: halogen or cyano, or $R^3$ and $R^4$ together with the nitrogen atom to which they are bonded represent a five- to ten-membered heterocycle which can optionally contain 1 or 2 further hetero atoms, in particular nitrogen, oxygen and/or sulphur, and which is optionally monosubstituted or polysubstituted by identical or different substituents, suitable substituents being: halogen, and in each case straight-chain or branched alkyl or halogenoalkyl, in each case having 1 to 4 carbon atoms and where appropriate 1 to 9 identical or different halogen atoms as well as 1 to 2 oxo or thiono groups, with the exception of the compounds which are individually listed in application Ser. No. 324,361, supra in which a) $R^1=CH_3$, $R^2=CH_3$, $R^3=H$, $R^4=$cyclohexyl;
b) $R^1=CH_3$, $R^2=C_2H_5$, $R^3=H$, $R^4=CH_2-C(CH_3)_3$;
c) $R^1=CH_3$, $R^2=C_2H_5$, $R^3=H$, $R^4=$1-phenyl-ethyl;
d) $R^1=C_2H_5$, $R^2=CH_3$, $R^3=H$, $R^4=C(CH_3)_3$;
e) $R^1=CH_3$, $R^2=CH_3$, $R^3=CH_3$, $R^4=C(CH_3)_3$;
f) $R^1=CH_3$, $R^2=CH_3$, $R^3=H$, $R^4=-CH(CH_3)-CH=N-OCH_3$ and
g) $R^1=CH_3$, $R^2=CH_3$, $R^3=H$,

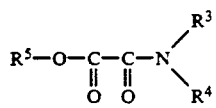

Furthermore, it has been found that the new compounds of the general formula (I) are obtained when
(a) amino guanidines of the general formula (II)

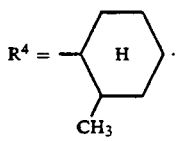

in which $R^1$ and $R^2$ have the abovementioned meanings, and/or tautomers of the compounds of the formula (II) and/or acid adducts of compounds of the formula (II) or of tautomers thereof, are reacted with oxalamidates of the general formula (III)

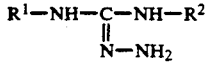

in which $R^3$ and $R^4$ have the abovementioned meanings and $R^5$ represents alkyl, if appropriate in the presence of a diluent and if appropriate in the presence of a reaction auxiliary, or when (b) chloroformamidine hydrochlorides of the general formula (IV)

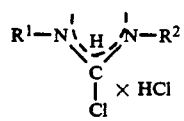

in which $R^1$ and $R^2$ have the abovementioned meanings, are reacted with oxamic acid hydrazides of the general formula (V)

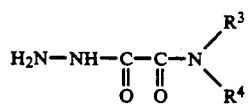

in which $R^3$ and $R^4$ have the abovementioned meanings, if appropriate in the presence of a diluent and if appropriate in the presence of an acid acceptor, or when (c) carbodiimides of the general formula (VI)

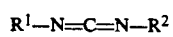

in which $R^1$ and $R^2$ have the abovementioned meanings, are reacted with oxamic acid hydrazides of the general formula (V)

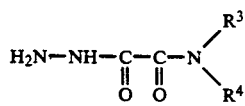

in which $R^3$ and $R^4$ have the abovementioned meanings, if appropriate in the presence of a diluent and if appropriate in the presence of a reaction auxiliary.

Finally, it has been found that the new 3-amino-5-aminocarbonyl-1,2,4-triazole derivatives of the general formula (I) have interesting herbicidal properties.

For example, the new 3-amino-5-aminocarbonyl-1,2,4-triazole derivatives of the general formula (I) have an excellent action against problem weeds combined with good to very good tolerance by crop plants.

Formula (I) provides a general definition of the 3-amino-5-aminocarbonyl-1,2,4-triazole derivatives according to the invention. Preferred compounds of the formula (I) are those in which $R^1$ represents methyl, ethyl, n- or i-propyl, n-, i-, s- or t-butyl, n- or i-pentyl, allyl, propargyl, or represents in each case straight-chain or branched halogenoalkyl having 1 to 4 carbon atoms, halogenoalkenyl having 3 to 6 carbon atoms or halogenoalkinyl having 3 to 6 carbon atoms and in each case 1 to 9 identical or different halogen atoms, or represents methoxymethyl, methoxyethyl, ethoxymethyl or ethoxyethyl, or represents cyclopropyl, cyclopropylmethyl, cyclopentyl, cyclohexyl, cyclohexylmethyl, cyclohexylethyl or cyclopentylmethyl, or represents benzyl, phenylethyl or phenyl, each of which is optionally monosubstituted to trisubstituted by identical or different substituents, suitable substituents in each case being: fluorine, chlorine, bromine, cyano, nitro, methyl, ethyl, n- or i-propyl, n-, i-, s- or t-butyl, methoxy, ethoxy, methylthio, trifluoromethyl, trifluoromethoxy or trifluoromethylthio, R² represents methyl, ethyl, n- or i-propyl, n-, i-, s- or t-butyl, n- or i-pentyl or n- or i-hexyl, or represents allyl or propargyl, or represents methoxymethyl, methoxyethyl, ethoxymethyl or ethoxyethyl, or represents a straight-chain or branched halogenoalkyl having 1 to 4 carbon atoms and 1 to 9 identical or different halogen atoms, in particular fluorine, chlorine or bromine, or represents cyclopentyl, cyclohexyl, cyclopropyl, cyclopropylmethyl, cyclohexylmethyl or cyclohexylethyl, or represents benzyl or phenyl, each of which is optionally monosubstituted to trisubstituted by identical or different substituents, suitable substituents in each case being: fluorine, chlorine, bromine, cyano, nitro, methyl, ethyl, n- or i-propyl, n-, i-, s- or t-butyl, methoxy, ethoxy, methylthio, trifluoromethyl, trifluoromethoxy or trifluoromethylthio, and R³ and R⁴ independently of one another in each case represent hydrogen, methyl, ethyl, n- or i-propyl, n-, i-, s- or t-butyl, in each case straight chain or branched pentyl, hexyl, heptyl, octyl, nonyl, decyl or dodecyl, or represent allyl, n- or i-butenyl, n- or i-pentenyl, n- or i-hexenyl, propargyl, n- or i-butinyl, n- or i-pentinyl or n- or i-hexinyl, or represent straight-chain or branched halogenoalkyl having 1 to 6 carbon atoms and 1 to 9 identical or different halogen atoms, in particular fluorine, chlorine or bromine, or represent in each case straight-chain or branched halogenoalkenyl or halogenoalkinyl, in each case having 3 to 5 carbon atoms and 1 to 3 halogen atoms, in particular fluorine or chlorine, or represent in each case straight-chain or branched cyanoalkyl having 1 to 6 carbon atoms in the alkyl moiety, hydroxyalkyl having 1 to 6 carbon atoms and 1 to 3 hydroxyl groups, alkoxyalkyl, alkoximinoalkyl, alkoxycarbonylalkyl or alkoxycarbonylalkenyl, alkylaminoalkyl or dialkylaminoalkyl, in each case having up to 4 carbon atoms in the individual alkyl moieties, or alkenyl moieties, or represent cyclopropyl, cyclopropylmethyl, cyclopropylethyl, cyclobutyl, cyclopentyl, cyclohexyl, cycloheptyl, cyclooctyl, cyclohexylmethyl, cyclohexylethyl, cyclohexenyl, cyclohexenylmethyl or cyclohexenylethyl, each of which is optionally monosubstituted to pentasubstituted by identical or different substituents, suitable substituents in each case being: fluorine, chlorine, bromine, methyl, ethyl, n- or i-propyl, n-, i-, s- or t-butyl, cyano, methanediyl, ethanediyl, butanediyl or butadienediyl; R³ and R⁴ furthermore independently of one another represent heterocyclylmethyl, heterocyclylpropyl or heterocyclylethyl, each of which is optionally monosubstituted to trisubstituted in the heterocyclyl moiety by identical or different substituents, suitable heterocycles in each case being:

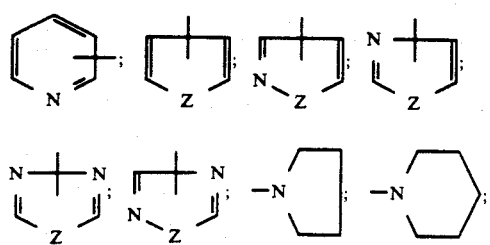

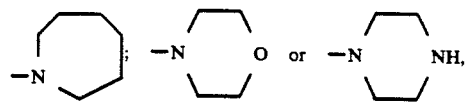

Z in each case representing oxygen or sulphur and suitable substituents in each case being: fluorine, chlorine, bromine, cyano, nitro, methyl, ethyl, n- or i-propyl, n-, i-, s- or t-butyl, methoxy, ethoxy, methylthio, trifluoromethyl, trifluoromethoxy or trifluoromethylthio; R³ and R⁴ furthermore independently of one another represent benzyl, phenylethyl, phenylpropyl, phenylbutyl, phenylpentyl, phenylhexyl, phenylheptyl, phenylcyanomethyl, phenylcyanoethyl, phenylcyanopropyl, benzoyl, phenyl or naphthyl, each of which is straight-chain or branched in the alkyl moiety (where appropriate), and each of which is optionally monosubstituted to trisubstituted by identical or different substituents, suitable phenyl substituents in each case being: fluorine, chlorine, bromine, hydroxyl, cyano, nitro, methyl, ethyl, n- or i-propyl, n-, i-, s- or t-butyl, methoxy, ethoxy, methylthio, trifluoromethyl, trifluoromethoxy, trifluoromethylthio, trifluoromethylsulphinyl, trifluoromethylsulphonyl, methylsulphinyl, methylsulphonyl, acetyl, propionyl, methoxycarbonyl, ethoxycarbonyl, cyclohexyl or phenoxy, or R³ and R⁴ together with the nitrogen atom to which they are bonded represent a heterocycle of the formula

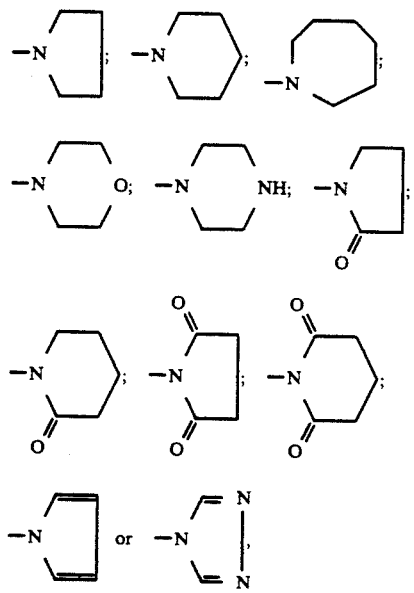

each of which is optionally monosubstituted to trisubstituted by identical or different substituents, suitable substituents in each case being: methyl, ethyl, n- or i-propyl, chloride or trifluoromethyl, with the exception of the compounds excluded above by the disclaimer.

Particularly preferred compounds of the formula (I) are those in which

R¹ represents methyl, ethyl, propyl, isopropyl or cyclohexyl,

R² represents methyl, ethyl, propyl, isopropyl or cyclohexyl,

R³ represents hydrogen or methyl,

R⁴ represents methyl, ethyl, n- or i-propyl, n-, i-, s- or t-butyl, n-, i-, s- or t-pentyl, n- or i-hexyl, n- or i-heptyl, n- or i-octyl, n- or i-nonyl, n- or i-decyl, n- or i-dodecyl, 1-ethyl-propyl, 1,2-dimethyl-propyl, 1,3-dimethyl-butyl, 1-methyl-1-ethyl-propyl, 1,1,3,3-tetramethyl-butyl or 1,2,2-trimethyl-propyl, or represents allyl, n- or i-butenyl, n- or i-pentenyl, n- or i-hexenyl, propargyl, n- or i-butinyl, n- or i-pentinyl or n- or i-hexinyl, or represents straight-chain or branched halogenoalkyl having 1 to 6 carbon atoms and 1 to 9 identical or different halogen atoms, in particular fluorine or chlorine, or represents in each case straight-chain or branched halogenoalkenyl or halogenoalkinyl, in each case having 3 to 5 carbon atoms and 1 to 3 halogen atoms, in particular fluorine or chlorine, or represents in each case straight-chain or branched cyanoalkyl having 1 to 6 carbon atoms in the alkyl moiety, hydroxyalkyl having 1 to 6 carbon atoms and 1 to 3 hydroxyl groups, alkoxyalkyl, alkoximinoalkyl, alkoxycarbonylalkyl or alkoxycarbonylalkenyl, alkylaminoalkyl or dialkylaminoalkyl, in each case having up to 4 carbon atoms in the individual alkyl moieties, or alkenyl moieties, or represents cyclopropyl, cyclopropylmethyl, cyclopropylethyl, cyclobutyl, cyclopentyl, cyclohexyl, cycloheptyl, cyclooctyl, cyclohexylmethyl, cyclohexylethyl, cyclohexenyl, cyclohexenylmethyl or cyclohexenylethyl, each of which is optionally monosubstituted to tetrasubstituted by identical or different substituents from the series comprising fluorine, chlorine, bromine, methyl, ethyl, n- or i-propyl, n-, i-, s- or t-butyl, cyano, methanediyl, ethanediyl, butanediyl or butadienediyl; R⁴ furthermore represents heterocyclylmethyl, heterocyclylpropyl or heterocyclylethyl, each of which is optionally monosubstituted to trisubstituted in the heterocyclyl moiety by identical or different substituents from the series comprising fluorine, chlorine, bromine, cyano, nitro, methyl, ethyl, n- or i-propyl, n-, i-, s- or t-butyl, methoxy, ethoxy, methylthio, trifluoromethyl, trifluoromethoxy or trifluoromethylthio, suitable heterocycles in each case being:

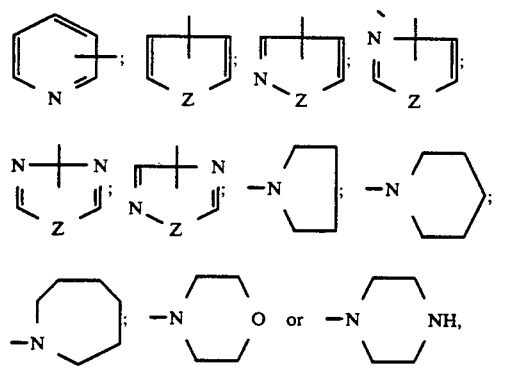

Z in each case representing oxygen or sulphur, R⁴ furthermore represents benzyl, phenylethyl, phenylpropyl, phenylbutyl, phenylpentyl, phenylhexyl, phenylheptyl, phenylcyanomethyl, phenylcyanoethyl, phenylcyanopropyl, benzoyl, phenyl or naphthyl, each of which is straight-chain or branched in the alkyl moiety (where appropriate), and each of which is optionally monosubstituted to trisubstituted in the phenyl moiety by identical or different substituents from the series comprising fluorine, chlorine, bromine, hydroxyl, cyano, nitro, methyl, ethyl, n- or i-propyl, n-, i-, s- or t-butyl, methoxy, ethoxy, methylthio, trifluoromethyl, trifluoromethoxy, trifluoromethylthio, trifluoromethylsulphinyl, trifluoromethylsulphonyl, methylsulphinyl, methylsulphonyl, acetyl, propionyl, methoxycarbonyl, ethoxycarbonyl, cyclohexyl or phenoxy, and R⁴ furthermore together with R³ can represent tetramethylene or pentamethylene, with the exception of the compounds excluded above by the disclaimer.

If, for example, 2-amino-1-ethyl-3-isopropylguanidine and O-methyl N,N-dimethyloxalamidate are used as starting substances, the course of the reaction in process (a) according to the invention may be represented by the following equation:

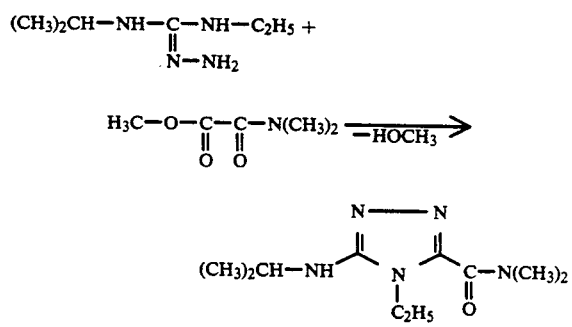

If, for example, chloro-dimethylformamidine hydrochloride and piperidino-oxalyl hydrazide are used as starting substances, the course of the reaction in process (b) according to the invention may be represented by the following equation:

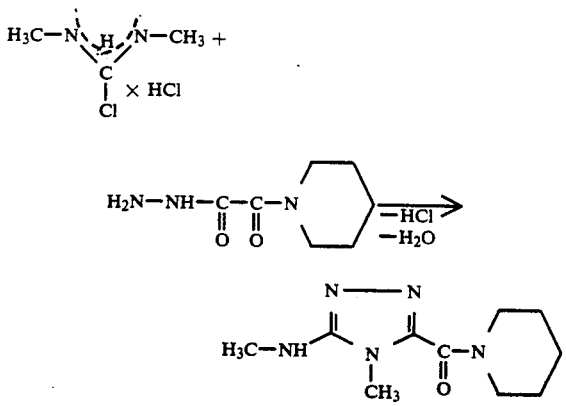

If, for example, dicyclohexylcarbodiimide and N-ethyloxamic acid hydrazide are used as starting substances, the course of the reaction in process (c) according to the invention may be represented by the following equation:

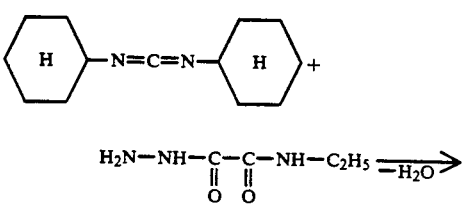

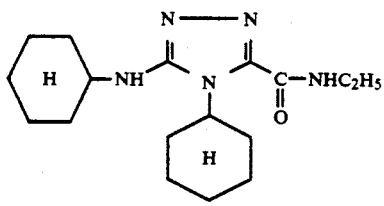

Formula (II) provides a general definition of the aminoguanidines to be used as starting substances in process (a) according to the invention for the preparation of compounds of the formula (I).

In formula (II), $R^1$ and $R^2$ preferably, or in particular, have those meanings which have already been mentioned above in connection with the description of the compounds of the formula (I) according to the invention as being preferred, or particularly preferred, for $R^1$ and $R^2$.

The preferred acid adducts of the compounds of the formula (II) are the hydrochlorides, hydrobromides or hydroiodides thereof.

The starting substances of the formula (II) and the acid adducts thereof are known and/or can be prepared by processes known per se (cf. J.Org.Chem. 19 (1954), 1807-1814; Bull. Soc. Chim. France 1975, 1649-1653).

For example, the compounds of the formula (II) are also obtained when 2-amino-1,1-dimethyl-guanidine derivatives of the general formula (VII)

in which $R^1$ has the abovementioned meaning, or tautomers of the compounds of the formula (VII) and/or acid adducts (preferably hydrochlorides, hydrobromides or hydroiodides) of compounds of the formula (VII) or of tautomers thereof, are reacted with amines of the general formula (VIII)

in which $R^2$ has the abovementioned meaning, in the presence of a diluent, such as, for example, isopropanol, at temperatures between 20° C. and 120° C. (cf. the Preparation Examples).

Formula (III) provides a general definition of the oxalamidates furthermore to be used as starting substances in process (a) according to the invention.

In formula (III), $R^3$ and $R^4$ preferably, or in particular, have those meanings which have already been mentioned above in connection with the description of the compounds of the formula (I) according to the invention as being preferred, or particularly preferred, for $R^3$ and $R^4$, and $R^5$ preferably represents $C_1$-$C_4$-alkyl, in particular methyl or ethyl.

The starting substances of the formula (III) are known and/or can be prepared by processes known per se (cf. DE-OS [German Published Specification] 2,819,878).

Formula (IV) provides a general definition of the chloroformamidine hydrochlorides to be used as starting substances in process (b) according to the invention for the preparation of compounds of the formula (I).

In formula (IV), $R^1$ and $R^2$ preferably, or in particular, have those meanings which have already been mentioned above in connection with the description of the compounds of the formula (I) according to the invention as being preferred, or particularly preferred, for $R^1$ and $R^2$.

The starting substances of the formula (IV) are known and/or can be prepared by processes known per se (cf. DE-OS [German Published Specification] 3,709,574, Chem. Ber. 97 (1964), 1232-1245)—cf. also the preparation examples.

Formula (V) provides a general definition of the axamic acid hydrazides to be used as starting substances in processes (b) and (c) according to the invention.

In formula (V), $R^3$ and $R^4$ preferably, or in particular, have those meanings which have already been mentioned above in connection with the description of the compounds of the formula (I) according to the invention as being preferred, or particularly preferred, for $R^3$ and $R^4$.

The starting substances of the formula (V) are known and/or can be prepared by processes known per se (cf. EP-A 126,326).

Formula (VI) provides a general definition of the carbodiimides to be used as starting substances in process (c) according to the invention for the preparation of compounds of the formula (I).

In formula (VI), $R^1$ and $R^2$ preferably, or in particular, have those meanings which have already been mentioned above in connection with the description of the compounds of the formula (I) according to the invention as being preferred, or particularly preferred, for $R^1$ and $R^2$.

The starting substances of the formula (VI) are known chemicals for organic synthesis.

Suitable diluents for carrying out process (a) according to the invention are inert organic solvents. These include, in particular, aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform, carbon tetrachloride, ethers, such as diethyl ether, dioxane, tetrahydrofuran, ethyleneglycol dimethyl ether or ethylene glycol diethyl ether, nitriles, such as acetonitrile or propionitrile, amides, such as dimethylformamide, dimethylacetamide, N-methylformanilide, N-methylpyrrolidone or hexamethylphosphoric triamide, or alcohols, such as methanol, ethanol or propanol.

If appropriate, process (a) according to the invention is carried out in the presence of a suitable reaction auxiliary. Suitable reaction auxiliaries are all inorganic and organic bases which can customarily be used. The hydrides, hydroxides, amides, alcoholates, carbonates or hydrogen carbonates of alkali metals, such as, for example, sodium hydride, sodium amide, sodium hydroxide, sodium methylate, sodium ethylate, potassium t-butylate, sodium carbonate or sodium hydrogen carbonate, and also tertiary amines, such as, for example, triethylamine, N,N-dimethylaniline, pyridine, N,N-dimethylaminopyridine, diazabicyclooctane (DABCO), diazabicyclononene (DBN) or diazabicycloundecene (DBU), are preferably used.

When carrying out process (a) according to the invention, the reaction temperatures can be varied within a substantial range. In general, the process is carried out at temperatures between 30° C. and 150° C., preferably at temperatures between 50° C. and 80° C.

For carrying out process (a) according to the invention, 0.8 to 1.5 moles, preferably 0.8 to 1.2 moles, of oxalamidate of the formula (III) and if appropriate 1 to 5 moles, preferably 1 to 2.5 moles, of reaction auxiliary are generally employed per mole of aminoguanidine of the formula (II) or of a corresponding acid addition salt. The reaction is carried out and the reaction products are worked up and isolated by generally customary methods (cf. also the preparation examples).

If appropriate, process (b) according to the invention is carried out in the presence of a diluent. Diluents which are preferably employed are polar organic solvents and/or water. Preferred organic solvents are alcohols, such as methanol, ethanol, propanol, isopropanol and butanol, ethers, such as ethylene glycol dimethyl ether, diethylene glycol dimethyl ether, tetrahydrofuran and dioxane, ether alcohols, such as ethylene glycol monomethyl ether and ethylene glycol monoethyl ether, amides, such as formamide and dimethylformamide, nitriles, and such as acetonitrile, propionitrile or benzonitrile, and also pyridine.

Acid acceptors which can be employed in process (b) according to the invention are all acid-binding agents which can customarily be used for reactions of this type. The following are preferably suitable alkali metal hydroxides, such as, for example, sodium hydroxide and potassium hydroxide, alkaline earth metal hydroxides, such as, for example, calcium hydroxide, alkali metal carbonates and alkali metal alcoholates, such as sodium carbonate and potassium carbonate, sodium methylate and potassium methylate, and furthermore aliphatic, aromatic or heterocyclic amines, for example triethylamine, trimethylamine, dimethylaniline, dimethylbenzylamine, pyridine, 1,5-diazabicyclo-[4,3,0]-non-5-ene (DBN),-1,8-diazabicyclo-[5,4,0]-undec-7-ene (DBU) and 1,4-diazabicyclo-[2,2,2]-octane (DABCO).

When carrying out process (b) according to the invention, the reaction temperatures can be varied within a substantial range. In general, the process is carried out at temperatures between 0° C. and 150° C., preferably at temperatures between 10° C. and 120° C.

In general, process (b) according to the invention is carried out under atmospheric pressure. However, it is also possible to carry out the process under increased or reduced pressure.

For carrying out process (b) according to the invention, between 0.5 and 1.5 moles, preferably between 0.8 and 1.2 moles, of oxamic acid hydrazide of the formula (V) and between 1 and 5 mole equivalents, preferably between 2 and 3 mole equivalents, of an acid acceptor are generally employed per mole of chloroformamidine hydrochloride of the formula (IV).

In general, the reactants of the formula (II) and (III) are mixed with the diluent at room temperature, an acid acceptor is added, and the mixture is then stirred until the reaction is complete, if appropriate at an increased temperature.

The reaction products can be worked up by customary methods (cf. the preparation examples).

If approprriate, process (c) according to the invention is carried out in the presence of a diluent. The same diluents can be used for this purpose as have been mentioned above in processes (a) and (b) according to the invention.

If appropriate, process (c) is carried out in the presence of a reaction auxiliary. The same reaction auxiliaries can be employed for this purpose as have been mentioned above in process (a) according to the invention.

When carrying out process (c) according to the invention, the reaction temperatures can be varied within a substantial range. In general, the process is carried out at temperatures between 0° C. and 150° C., preferably at temperatures between 20° C. and 120° C.

In general, process (c) according to the invention is carried out under atmospheric pressure. However, it is also possible to carry out the process under increased or reduced pressure.

For carrying out process (c) according to the invention, the specifically required starting substances are generally employed in approximately equimolar amounts. However, it is also possible to use one of the two specifically employed components in a substantial excess. In general, the reactions are carried out in a suitable diluent, and the reaction mixture is stirred for several hours at the particular required temperature. The reaction products in process (c) according to the invention are worked up in each case by customary methods (cf. the preparation examples).

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The compounds of the formula (I) according to the invention are particularly suitable for selectively combating dicotyledon weeds in monycotyledon crops, such as, for example, in corn, in both the pre-emergence and the post-emergence method.

To a certain extent, the compounds of the formula (I) also show a fungicidal action, such as, for example, against apple scab (*Venturia inaequalis*).

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene, or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example lignin-sulphite waste liquors and methylcellulose.

Adhesives, such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

For combating weeds, the active compounds according to the invention, as such or in the form of their formulations, can also be used as mixtures with known herbicides, finished formulations or tank mixes being possible.

Suitable herbicides for the mixtures are known herbicides, such as, for example, 1-amino-6-ethylthio-3-(2,2-dimethylpropyl)-1,3,5-triazine-2,4(1H,3H)-dione (AMETHYDIONE) or N-(2-benzothiazolyl)-N,N'-dimethyl-urea (METABENZTHIAZURON) for combating weeds in cereals; 4-amino-3-methyl-6-phenyl-1,2,4-triazin-5(4H)-one (METAMITRON) for combating weeds in sugar beets, and 4-amino-6-(1,1-dimethylethyl)-3-methylthio-1,2,4-triazin-5(4H)-one (METRIBUZIN) for combating weeds in soy, by means furthermore also 2,4-dichlorophenoxyacetic acid (2,4-D); 4-(2,4-dichlorophenoxy)-butyric acid (2,4-DB); 2-chloro2',6'-diethyl-N-methoxymethyl-acetanilide (ALACHLOR); 2-chloro-4-ethylamino-6-isopropylamino-1,3,5-triazine (ATRAZINE); 3-isopropyl-1,3-benzothiadiazin-4-one 2,2-dioxide (BENTAZONE); 3,5-dibromo-4-hydroxy-benzonitrile (BROMOXYNIL); 2-chloro-4-ethylamino-6-(3-cyanopropylamino)-1,3,5-triazine (CYANAZINE); 4-amino-6-t-butyl-3-ethylthio-1,2,4-triazin-5(4H)-one (ETHIOZIN); 3,5-diiodo-4-hydroxybenzonitrile (IOXYNIL); N-methyl-2-(1,3-benzothiazol-2-yloxy)-acetanilide (MEFENACET); 2-chloro-N-(2,6-dimethylphenyl)-N-[(1H)-pyrazol-1-yl-methyl]-acetamide (METAZACHLOR); 2-ethyl-6-methyl-N-(1-methyl-2-methoxyethyl)-chloroacetanilide (METOLACHLOR); N-(1-ethylpropyl)-3,4-dimethyl-2,6-dinitroaniline (PENDIMETHALIN); S-octyl 0-(6-chloro-3-phenylpyridazin-4-yl) thiocarbonate (PYRIDATE) and methyl 3-[[[[(4-methoxy-6-methyl-1,3,5-triazin- 2-yl)-amino]-carbonyl]-amino]-sulfonyl]-thiophene-2-carboxylate (THIAMETURON). Surprisingly, some mixtures also show synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and use of the active compounds according to the invention can be seen from the following examples.

PREPARATION EXAMPLES

Example 1

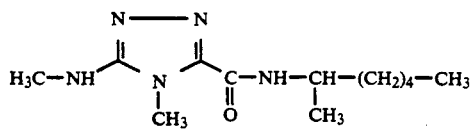

Process (a)

A mixture of 24.8 g (0.18 mol) of 2-amino-1,3-dimethyl-guanidine hydrochloride, 32.9 g (0.15 mol) of O-ethyl N-sec-heptyloxalamidate, 16.2 g (0.3 mol) of sodium methylate and 200 ml of methanol is stirred for 3 hours at reflux temperature. The mixture is subsequently cooled to room temperature and filtered. The filtrate is concentrated under a water pump vacuum, the residue is taken up in 200 ml of dichloromethane, and the mixture is washed three times with 100 ml portions of water in each case, dried over sodium sulphate and filtered. The solvent is removed from the filtrate by distillation under a water pump vacuum.

This gives 24.8 g (65% of theory) of N-sec-heptyl 5-methylamino-4-methyl-4H-1,2,4-triazol-3-yl-carboxamidate of melting point 101° C.-103° C.

Example 2

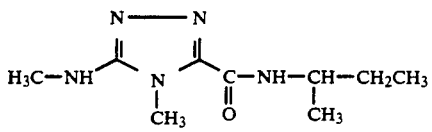

Process (b)

A mixture of 7.15 g (0.05 mol) of chloro-N,N'-dimethylformamidine hydrochloride, 7.9 g (0.05 mol) of N-sec-butyl-oxamic acid hydrazide, 5.4 g (0.1 mol) of sodium methylate and 200 ml of butanol is stirred at reflux temperature for 60 minutes. The mixture is subsequently cooled to room temperature and filtered. The filtrate is concentrated under a water pump vacuum, the residue is taken up in 150 ml of dichloromethane, and the mixture is washed three times with 100 ml portions of water in each case, dried over sodium sulphate and filtered. The solvent is removed from the filtrate by distillation under a water pump vacuum.

This gives 4.4 g (40% of theory) of N-sec-butyl 5-methylamino-4-methyl-4H-1,2,4-trizol-3-yl-carboxamidate of melting point 129° C.-131° C.

Example 3

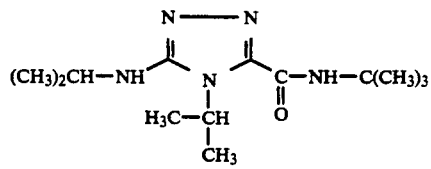

Process (c)

A mixture of 12.6 g (0.1 mol) of N,N'-diisopropylcarbodiimide, 15.9 g (0.1 mol) of N-tert-butyloxamic acid hydrazide, 0.8 g of sodium methylate and 200 ml of butanol is stirred for 3 hours at reflux temperature, then cooled to room temperature and filtered. The filtrate is concentrated under a water pump vacuum, the residue is taken up in 200 ml of dichloromethane, and the mixture is washed three times with 100 ml portions of water in each case, dried over sodium sulphate and filtered. The solvent is removed from the filtrate by distillation under a water pump vacuum. The crude product obtained as the residue is purified by column chromatography (silica gel; cyclohexane/ethanol 1 :1) and recrystallised from cyclohexane.

This gives 8.7 g (33% of theory) of N-tertbutyl-5-isopropylamino-4-isoprop-yl-4H-1,2,4-trizol-3-yl-carboxamidate of melting point 135°-137° C.

For example, the compounds of the formula (I) listed in Table 1 below can also be prepared analogously to Examples 1 to 3 and following the general description of the preparation processes according to the invention.

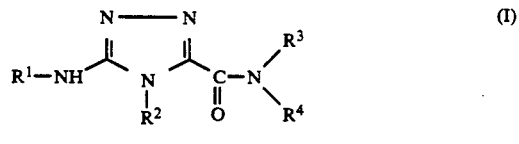

(I)

TABLE 1

| Examples of the compounds of the formula (I) | | | | | |
|---|---|---|---|---|---|
| Example no. | R¹ | R² | R³ | R⁴ | Melting point (°C.) |
| 4 | CH₃ | CH₃ | H | —C(CH₃)₃ | 166–167 |
| 5 | CH₃ | CH₃ | H | —CH(C₂H₅)₂ | 141–143 |
| 6 | CH₃ | CH₃ | H | —CH(CH₃)—CH(CH₃)₂ | 130–132 |
| 7 | CH₃ | CH₃ | H | —CH₂CH=CH₂ | 125–127 |
| 8 | CH₃ | CH₃ | H | —CH(CH₃)₂ | 122–124 |
| 9 | CH₃ | CH₃ | H | cyclohexyl-CH₃ | 132–133 |

TABLE 1-continued

Examples of the compounds of the formula (I)

| Example no. | R¹ | R² | R³ | R⁴ | Melting point (°C.) |
|---|---|---|---|---|---|
| 10 | CH₃ | CH₃ | H | —CH₂—(cyclohexyl, H) 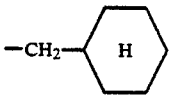 | 146–148 |
| 11 | CH₃ | CH₃ | H | —CH(CH₃)—(cyclohexenyl) 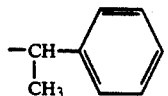 | 118–120 |
| 12 | CH₃ | CH₃ | H | —C(CH₃)(CH₂F)(CH₂F) 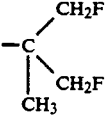 | 159–160 |
| 13 | CH₃ | CH₃ | H | —CH₂CH₂Cl | 221–223 |
| 14 | CH₃ | CH₃ | H | cyclopentyl  | 160–161 |
| 15 | CH₃ | CH₃ | H | —CH₂CH(CH₃)CH₂CH₃ | 79–81 |
| 16 | CH₃ | CH₃ | H | —CH₂CH(CH₃)₂ | 116–118 |
| 17 | CH₃ | CH₃ | H | —C(CH₃)(CH₃)—CH₂CH₃  | 150–152 |
| 18 | CH₃ | CH₃ | H | phenyl  | 219–221 |
| 19 | CH₃ | CH₃ | H | —CH₂—(2-chlorophenyl)  | 150–152 |
| 20 | CH₃ | CH₃ | H | —CH(CH₃)CH₂CH₂CH₃ | 118–120 |
| 21 | CH₃ | CH₃ | H | 3,3,5-trimethylcyclohexyl  | 152 |
| 22 | CH₃ | CH₃ | H | 4-methylcyclohexyl 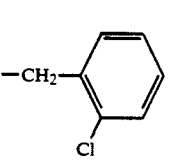 | 137–139 |
| 23 | CH₃ | CH₃ | H | 4-methylcyclohexyl 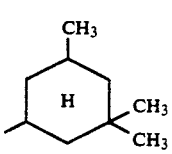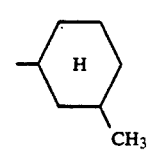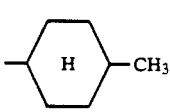 | 132–134 |

TABLE 1-continued

Examples of the compounds of the formula (I)

| Example no. | R¹ | R² | R³ | R⁴ | Melting point (°C.) |
|---|---|---|---|---|---|
| 24 | CH₃ | CH₃ | H | −C(C₂H₅)(C₂H₅)(CH₃) | 115–117 |
| 25 | CH₃ | CH₃ | H | −C(CH₃)(CH₃)−CH₂C(CH₃)₃ | 97–99 |
| 26 | CH₃ | CH₃ | H | −C(CH₃)(CH₃)−CH₂F | 124–126 |
| 27 | CH₃ | CH₃ | H | −CH(CH₃)−C(CH₃)₃ | 90–92 |
| 28 | CH₃ | CH₃ | H | −C(CH₃)(CH₃)−CF₃ | 191–193 |
| 29 | CH₃ | CH₃ | H | (cyclobutyl with CH₃, F, F, Cl, F substituents) | 109–111 |
| 30 | CH₃ | CH₃ | H | −CH(CH₃)−CH₂−CH(CH₃)₂ | 114–116 |
| 31 | CH₃ | CH₃ | H | −CH₂CH₂CH₂CH₃ | 118–120 |
| 32 | CH₃ | CH₃ | H | −C(CH₃)₃ | 245–247 |
| 33 | cyclohexyl-H | cyclohexyl-H | H | −C(CH₃)₃ | 250 |
| 34 | CH₃ | CH₃ |  | −(CH₂)₅− | ¹H-NMR (DMSO-D⁶, δ, ppm); 1.50–1.65; 2.80; 6.25. |

STARTING SUBSTANCES OF THE FORMULA (II)

Example (II-1)

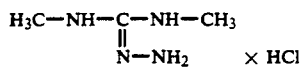

152.5 g (1.0 mol) of 2-amino-1,1,3-trimethylguanidine hydrochloride are refluxed in 2.0 liters of isopropanol. During this process, 155 g (5 mol) of methylamine are introduced in the course of 2 hours. The mixture is cooled to 15° C., and the product obtained in crystalline form is then isolated by filtration with suction.

This gives 98.2 g (71% of theory) of 2-amino-1,3-dimethyl-guanidine hydrochloride of melting point 250° C. ¹H-NMR (DMSO-D⁶, δ, ppm): 2.7–2.8.

STARTING SUBSTANCES OF THE FORMULA (IV)

Example (IV-1)

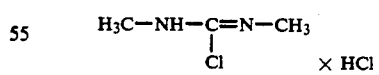

110 g (1.1 mol) of phosgene are passed at 80° C. within 1.5 hours into a mixture of 88 g (1 mol) of N,N'-dimethylurea and 500 ml of chlorobenzene, and, when the passing-in of gas has been completed, stirring of the mixture at 80° C. is continued for a further 45 minutes until the evolution of carbon dioxide has ceased. The reaction mixture is cooled under nitrogen, and the solids are filtered off with suction under nitrogen at 20° C. To purify the solid product which is obtained on evaporation of the filtrate, it is dissolved in chloroform and precipitated using tetrahydrofuran.

This gives 34 g (24% of theory) of N,N'-dimethyl-chloroformamidine hydrochloride of melting point 156° C.-158° C.

USE EXAMPLES

Example A

Pre-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added, and the concentrate is diluted with water to the desired concentration.

Seeds of the test plants are sown in normal soil and, after 24 hours, watered with the preparation of active compound. It is expedient in this context to keep constant the amount of water per unit area. The concentration of active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, an excellent effectiveness in combating weeds, in particular dicotyledon weeds, combined with a good selectivity in crop plants, is shown, for example, by the compounds of Preparation Examples 2, 4, 5, 6, 8, 9, 11, 12, 15, 16, 17, 20, 22, 23 and 34.

Example B

Post-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0% = no action (like untreated control)
100% = total destruction

In this test, an excellent herbicidal action in combating weeds, in particular dicotyledon weeds, combined with a good selectivity in crop plants, is shown, for example, by the compounds of Preparation Examples 1, 2, 4, 5, 6, 7, 8, 9, 10, 11, 12, 14, 15, 16, 17, 18, 19, 20, 22, 23, 24 and 34.

It will be appreciated that the instant specification is set forth by way of illustration and not limitation, and that various modifications and changes may be made without departing from the spirit and scope of the present invention.

What is claimed is:

1. A 3-amino-5-aminocarbonyl-1,2,4-triazole of the formula $$R^1-NH-C(=N-N)-N(R^2)-C(=N)-C(=O)-N(R^3)(R^4) \quad (I)$$

in which $R^1$ represents in each case straight-chain or branched alkyl having 1 to 8 carbon atoms, alkenyl having 2 to 8 carbon atoms, alkinyl having 2 to 8 carbon atoms, halogenoalkyl having 1 to 8 carbon atoms and 1 to 17 identical or different halogen atoms, halogenoalkenyl having 2 to 8 carbon atoms and 1 to 15 identical or different halogen atoms, or halogenoalkinyl having 2 to 8 carbon atoms and 1 to 13 identical or different halogen atoms, alkoxyalkyl having 1 to 6 carbon atoms in the individual alkyl moieties, or represents cycloalkyl having 3 to 7 carbon atoms, or represents cycloalkylalkyl having 3 to 7 carbon atoms in the cycloalkyl moiety and 1 to 6 carbon atoms in the straight-chain or branched alkyl moiety, or represents aralkyl which has 6 to 10 carbon atoms in the aryl moiety and 1 or 6 carbon atoms in the straight-chain or branched alkyl moiety and which is optionally monosubstituted or polysubstituted by identical or different substituents, or aryl which has 6 or 10 carbon atoms and which is optionally monosubstituted or polysubstituted by identical or different substituents, the substituents in each case being selected from the group consisting of halogen, cyano, nitro and straight-chain or branched alkyl, alkoxy, alkylthio, halogenoalkyl, halogenoalkoxy or halogenoalkylthio, in each case having 1 to 4 carbon atoms and where appropriate 1 to 9 identical or different halogen atoms, $R^2$ represents in each case straight-chain or branched alkyl having 1 to 8 carbon atoms, alkenyl having 2 to 8 carbon atoms, alkinyl having 2 to 8 carbon atoms, halogenoalkyl having 1 to 8 carbon atoms and 1 to 17 identical or different halogen atoms, halogenoalkenyl having 2 to 8 carbon atoms and 1 to 15 identical or different halogen atoms, or halogenoalkinyl having 2 to 8 carbon atoms and 1 to 13 identical or different halogen atoms, alkoxyalkyl having 1 to 6 carbon atoms in the individual alkyl moieties, or represents cycloalkylalkyl or cycloalkyl, in each case having 3 to 7 carbon atoms in the cycloalkyl moiety and where appropriate 1 to 6 carbon atoms in the straight-chain or branched alkyl moiety, or represents aralkyl or aryl, each of which has 6 to 10 carbon atoms in the aryl moiety and where appropriate 1 or 6 carbon atoms in the straight-chain or branched alkyl moiety and each of which is optionally monosubstituted or polysubstituted by identical or different substituents, the aryl substituents in each case being selected from the group consisting of halogen, cyano, nitro and straight-chain or branched alkyl, alkoxy, alkylthio, halogenoalkyl, halogenoalkoxy or halogenoalkylthio, in each case having 1 to 4 carbon atoms and where appropriate 1 to 9 identical or different halogen atoms, and $R^3$ and $R^4$ independently of one another in each case represent hydrogen, or in each case represent straight-chain or branched alkyl having 1 to 18 carbon atoms, alkenyl having 2 to 8 carbon atoms, alkinyl having 2 to 8 carbon atoms, halogenoalkyl having 1 to 8 carbon atoms and 1 to 17 identical or different halogen atoms, halogenoalkenyl or halogenoalkinyl, in each case having 2 to 8 carbon atoms and 1 to 15, or 13, identical or different halogen atoms, or cyanoalkyl having 1 to 8 carbon atoms, hydroxyalkyl having 1 to 8 carbon atoms and 1 to 6 hydroxyl groups, or alkoxyalkyl, alkoxyiminoalkyl, alkoxycarbonylalkyl or alkoxycarbonylalkenyl, in each case having up to 6 carbon atoms in the individual alkyl moieties, or alkenyl moieties, or alkylaminoalkyl or dialkyloaminoalkyl, in each case having 1 to 6 carbon atoms in the individual alkyl moieties, or cycloalkyl, cycloalkylalkyl, cycloalkenyl or cycloalkenylalkyl, each of which has 3 to 8 carbon atoms in the cycloalkyl moiety, or cycloalkenyl moiety, and where appropriate 1 to 6 carbon atoms in the straight-chain or branched alkyl moiety and each of which is optionally monosubstituted or polysubstituted by identical or different substituents, selected from the group consisting of halogen, cyano, and straight-chain or branched alkyl or halogenoalkyl, in each case having 1 to 4 carbon atoms and where appropriate 1 to 9 identical or different halogen atoms, or in each case double-linked alkanediyl, or alkenediyl, in each case having up to 4 carbon atoms; and $R^3$ and $R^4$ furthermore independently of one another represent aralkyl, aryl or aryl, each of which has 6 to 10 carbon atoms in the aryl moiety and where appropriate 1 to 8 carbon atoms in the straight-chain or branched alkyl moiety and each of which is optionally monosubstituted or polysubstituted by identical or different substituents, the aryl substituents in each case being selected from the group consisting of halogen, cyano, nitro hydroxyl, straight-chain or branched alkyl, alkoxy, alkythio, halogenoalkyl, halogenoalkoxy, halogenoalkylthio, alkylsulphinyl, alkylsulphonyl, halogenoalkylsulphinyl, halogenalkylsulphonyl, alkanoyl or alkoxycarbonyl, in each case having 1 to 6 carbon atoms and where appropriate 1 to 9 identical or different halogen atoms, cycloalkyl having 3 to 6 carbon atoms or phenoxy, and the alkyl substituents in each case being halogen or cyano, with the exception of the compounds in which
a) $R^1=CH_3$, $R^2=CH_3$, $R^3=H$, $R^4=$cyclohexyl;
b) $R^1=CH_3$, $R^2=C_2H_5$, $R^3=H$, $R^4=CH_2-C(CH_3)_3$;
c) $R^1=CH_3$, $R^2=C_2H_5$, $R^3=H$, $R^4=$1-phenyl-ethyl;
d) $R^1=C_2H_5$, $R^2=CH_3$, $R^3=H$, $R^4=C(CH_3)_3$;
e) $R^1=CH_3$, $R^2=CH_3$, $R^3=CH_3$, $R^4=C(CH_3)_3$;
f) $R^1=CH_3$, $R^2=CH_3$, $R^3=H$, $R^4=-CH(CH_3)-CH=N-OCH_3$ and
g) $R^1=CH_3$, $R^2=CH_3$, $R^3=H$,

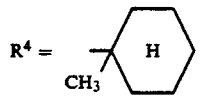

2. A 3-amino-5-aminocarbonyl-1,2,4-triazole according to claim 1, in which
$R^1$ represents methyl, ethyl, n- or i-propyl, n-, i-, s- or t-butyl, n- or i-pentyl, allyl, propargyl, or represents in each case straight-chain or branched halogenoalkyl having 1 to 4 carbon atoms, halogenoalkenyl having 3 to 6 carbon atoms or halogenalkinyl having 3 to 6 carbon atoms and in each case 1 to 9 identical or different halogen atoms, or represents methoxymethyl, methoxyethyl, ethoxymethyl or ethoxyethyl, or represents cyclopropyl, cyclopropylmethyl, cyclopentyl, cyclohexyl, cyclohexylmethyl, cyclohexylethyl or cyclopentylmethyl, or represents benzyl, phenylethyl or phenyl, each of which is optionally monosubstituted to trisubstituted by identical or different substituents selected from the group consisting of fluorine, chlorine, bromine, cyano, nitro, methyl, ethyl, n- or i-propyl, n-, i-, s- or t-butyl, methoxy, ethoxy, methylthio, trifluoromethyl, trifluoromethoxy and trifluoromethylthio, $R^2$ represents methyl, ethyl, n- or i-propyl, n-, i-, s- or t-butyl, n- or i-pentyl, or n- or i-hexyl, or represents allyl or propargyl, or represents methoxymethyl, methoxyethyl, ethoxymethyl or ethoxyethyl, or represents a straight-chain or branched halogenoalkyl having 1 to 4 carbon atoms and 1 to 9 identical or different halogen atoms, or represents cyclopentyl, cyclohexyl, cyclopropyl, cyclopropylmethyl, cyclohexylmethyl or cyclohexylethyl, or represents benzyl or phenyl, each of which is optionally monosubstituted to trisubstituted by identical or different substituents selected from the group consisting of fluorine, chlorine, bromine, cyano, nitro, methyl, ethyl, n- or i-propyl, n-, i-, s- or t-butyl, methoxy, ethoxy, methylthio, trifluoromethyl, trifluoromethoxy and trifluoromethylthio, and $R^3$ and $R^4$ independently of one another in each case represent hydrogen, methyl, ethyl, n- or i-propyl, n-, i-, s- or t-butyl, in each case straight-chain or branched pentyl, hexyl, heptyl, octyl, nonyl, decyl or dodecyl, or represent allyl, n- or i-butenyl, n- or i-pentenyl, n- or i-hexenyl, propargyl, n- or i-butinyl, n- or i-pentinyl or n- or i-hexinyl, or represent straight-chain or branched halogenoalkyl having 1 to 6 carbon atoms and 1 to 9 identical or different halogen atoms, or represent in each case straight-chain or branched halogenoalkenyl or halogenoalkinyl, in each case having 3 to 5 carbon atoms and 1 to 3 halogen atoms, or represent in each case straight-chain or branched cyanoalkyl having 1 to 6 carbon atoms in the alkyl moiety, hydroxyalkyl having 1 to 6 carbon atoms and 1 to 3 hydroxyl groups, alkoxyalkyl, alkoxyiminoalkyl, alkoxycarbonylalkyl or alkoxycarbonylalkenyl, alkylaminoalkyl or dialkyloaminoalkyl, in each case having up to 4 carbon atoms in the individual alkyl moieties, or alkenyl moieties, or represent cyclopropyl, cyclopropylmethyl, cyclopropylethyl, cyclobutyl, cyclopentyl, cyclohexyl, cycloheptyl, cyclooctyl, cyclohexylmethyl, cyclohexylethyl, cyclohexenyl, cyclohexenylmethyl or cyclohexenylethyl, each of which is optionally monosubstituted to pentasubstituted by identical or different substituents selected from the group consisting of fluorine, chlorine, bromine, methyl, ethyl, n- or i-propyl, n-, i-, s- or t-butyl, cyano, methanediyl, ethanediyl, butanediyl and butadienediyl; or $R^3$ and $R^4$ independently of one another represent benzyl, phenylethyl, phenylpropyl, phenylbutyl, phenylpentyl, phenylhexyl, phenylheptyl, phehylcyanomethyl, pheylcyanoethyl, phenylcyanopropyl, benzoyl, phenyl or naphthyl, each of which is straight-chain or branched in the alkyl moiety (where appropriate), and each of which is optionally monosubstituted to trisubstituted by identical or different substituents, the optional phenyl substituents in each case being selected from the group consisting of fluorine, chlorine, bromine, hydroxyl, cyano, nitro, methyl, ethyl, n- or i-propyl, n-, i-, s- or t-butyl, cyano, methoxy, ethoxy, methylthio, trifluoromethyl, trifluoromethoxy, trifluoromethylthio, trifluormethylsulphinyl, trifluoromethylsulphonyl, methylsulphinyl, methylsulphinyl, acetyl, propionyl, methoxycarbonyl, ethoxycarbonyl, cyclohexyl and phenoxy, with the exception of the compounds in which
a) $R^1=CH_3$, $R^2=CH_3$, $R^3=H$, $R^4=$cyclohexyl;
b) $R^1=CH_3$, $R^2=C_2H_5$, $R^3=H$, $R^4=CH_2-C(CH_3)_3$;
c) $R^1=CH_3$, $R^2=C_2H_5$, $R^3=H$, $R^4=$1-phenyl-ethyl;
d) $R^1=C_2H_5$, $R^2=CH_3$, $R^3=H$, $R^4=C(CH_3)_3$;
e) $R^1=CH_3$, $R^2=CH_3$, $R^3=CH_3$, $R^4=C(CH_3)_3$;
f) $R^1=CH_3$, $R^2=CH_3$, $R^3=H$, $R^4=-CH(CH_3)-CH=N-OCH_3$ and
g) $R^1=CH_3$, $R^2=CH_3$, $R^3=H$,

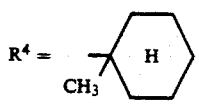

3. A 3-amino-5-aminocarbonyl-1,2,4-triazole according to claim 1, in which $R^1$ represents methyl, ethyl, propyl, isopropyl or cyclohexyl, $R^2$ represents methyl, ethyl, propyl, isopropyl or cyclohexyl, $R^3$ represents hydrogen or methyl, $R^4$ represents methyl, ethyl, n- or i-propyl, n-, i-, s- or t-butyl, n-, i-, s- or t-pentyl, n- or i-hexyl, n- or i-heptyl, n- or i-octyl, n- or i-nonyl, n- or i-decyl, n- or i-dodecyl, 1-ethyl-propyl, 1,2-dimethyl-propyl, 1,3-dimethyl-butyl, 1-methyl-1-ethyl-propyl, 1,1,3,3-tetramethyl-butyl or 1,2,2-trimethyl-propyl, or represents allyl, n- or i-butenyl, n- or i-pentenyl, n- or i-hexenyl, propargyl, n- or i-butinyl, n- or i-pentinyl or n- or i-hexinyl, or represents straight-chain or branched halogenoalkyl having 1 to 6 carbon atoms and 1 to 9 identical or different halogen atoms, or represent in each case straight-chain or branched halogenoalkenyl or halogenoalkinyl, in each case having 3 to 5 carbon atoms and 1 to 3 halogen atoms, or represents in each case straight-chain or branched cyanoalkyl having 1 to 6 carbon atoms in the alkyl moiety, hydroxyalkyl having 1 to 6 carbon atoms and 1 to 3 hydroxyl groups, alkoxyalkyl, alkoxyiminoalkyl, alkoxycarbonylalkyl or alkoxycarbonylalkenyl, alkylaminoalkyl or dialkyloaminoalkyl, in each case having up to 4 carbon atoms in the individual alkyl moieties, or alkenyl moieties, or represent cyclopropyl, cyclopropylmethyl, cyclopropylethyl, cyclobutyl, cyclopentyl, cyclohexyl, cycloheptyl, cyclooctyl, cyclohexylmethyl, cyclohexylethyl, cyclohexenyl, cyclohexenylmethyl or cyclohexenylethyl, each of which is optionally monosubstituted to tetrasubstituted by identical or different substituents selected from the group consisting of fluorine, chlorine, bromine, methyl, ethyl, n- or i-propyl, n-, i-, s- or t-butyl, cyano, methanediyl, ethanediyl, butanediyl and butadienediyl, or $R^4$ represent benzyl, phenylethyl, phenylpropyl, phenylbutyl, phenylpentyl, phenylhexyl, phenylheptyl, phehylcyanomethyl, pheylcyanoethyl, phenylcyanopropyl, benzoyl, phenyl or naphthyl, each of which is straight-chain or branched in the alkyl moiety (where appropriate), and each of which is optionally monosubstituted to trisubstituted in the phenyl moiety by identical or different substituents from the group consisting of fluorine, chlorine, bromine, hydroxyl, cyano, nitro, methyl, ethyl, n- or i-propyl, n-, i-, s- or t-butyl, methoxy, ethoxy, methylthio, trifluoromethyl, trifluoromethoxy, trifluoromethylthio, trifluormethylsulphinyl, trifluoromethylsulphonyl, methylsulphinyl, methylsulphinyl, acetyl, propionyl, methoxycarbonyl, ethoxycarbonyl, cyclohexyl and phenoxy, with the exception of the compounds in which
a) $R^1=CH_3$, $R^2=CH_3$, $R^3=H$, $R^4=$cyclohexyl;
b) $R^1=CH_3$, $R^2=C_2H_5$, $R^3=H$, $R^4=CH_2-C(CH_3)_3$;
c) $R^1=CH_3$, $R^2=C_2H_5$, $R^3=H$, $R^4=$1-phenyl-ethyl;
d) $R^1=C_2H_5$, $R^2=CH_3$, $R^3=H$, $R^4=C(CH_3)_3$;
e) $R^1=CH_3$, $R^2=CH_3$, $R^3=CH_3$, $R^4=C(CH_3)_3$;
f) $R^1=CH_3$, $R^2=CH_3$, $R^3=H$, $R^4=-CH(CH_3)-CH=N-OCH_3$ and
g) $R^1=CH_3$, $R^2=CH_3$, $R^3=H$,

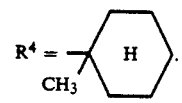

4. A compound according to claim 1, wherein such compound is N-isopropyl-5-methylamino-4-methyl-4H-1,2,4-triazol-3-yl-carboxamidate of the formula

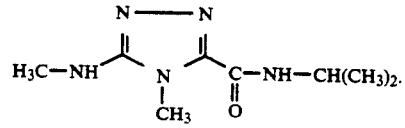

5. A compound according to claim 1, wherein such compound is N-(2-methyl-cyclohexyl)-5-methylamino-4-methyl-4H-1,2,4-triazol-3-yl-carbooxamidate of the formula

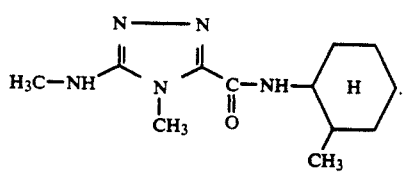

6. A compound according to claim 1, wherein such compound is N-cyclohexylmethyl-5-methylamino-4-methyl-4H-1,2,4-triazol-3-yl-carboxamidate of the formula

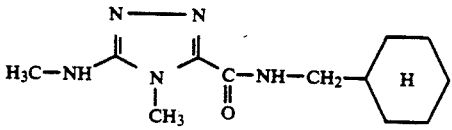

7. A compound according to claim 1, wherein such compound is N-(1,1-bis-fluoromethyl-ethyl)-5-methylamino-4-methyl-4H-1,2,4-triazol-3-yl-carboxamidate of the formula

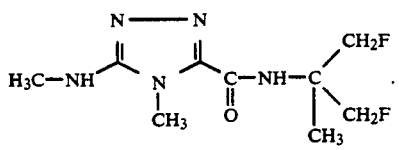

8. A compound according to claim 1, wherein such compound is N-(2-methyl-propyl)-5-methylamino-4-methyl-4H-1,2,4-triazol-3-yl-carboxamidate of the formula

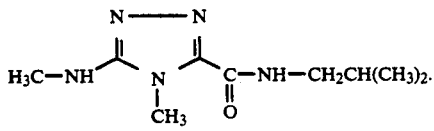

9. A compound according to claim 1, wherein such compound is N-phenyl-5-methylamino-4-methyl-4H-1,2,4-triazol-3-yl-carboxamidate of the formula

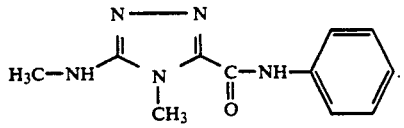

10. A compound according to claim 1, wherein such compound is N-(2-chloro-benzyl)-5-methylamino-4-methyl-4H-1,2,4-triazol-3-yl-carboxamidate of the formula

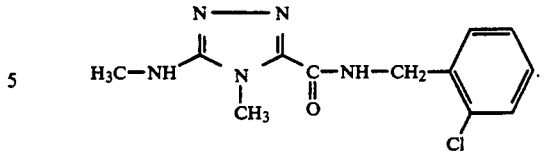

11. A herbicidal composition comprising a herbicidally effective amount of an compound according to claim 1 and an inert diluent.

12. A method of combating unwanted vegetation which comprises applying to such vegetation or to a locus from which it is desired to exclude such vegetation a herbicidally effective amount of a compound according to claim 1.

13. The method according to claim 12, wherein such compound is
N-isopropyl-5-methylamino-4-methyl-4H-1,2,4-triazol-3-yl-carboxamidate,
N-(2-methyl-cyclohexyl)-5-methylamino-4-methyl-4H-1,2,4-triazol-3-yl-carboxamidate,
N-cyclohexylmethyl-5-methylylamino-4-methyl-4H-1,2,4-triazol-3-yl-carboxamidate,
N-1,1-bis-fluoromethyl-ethyl)-5-methylamino-4-methyl-4H-1,2,4-triazol-3-yl-carboxamidate,
N-(2-methyl-propyl)-5-methylamino-4-methyl-4H-1,2,4-triazol-3-yl-carboxamidate,
N-phenyl-5-methylamino-4-methyl-4H-1,2,4-triazol-3-yl-carboxamidate, or
N-(2-chloro-benzyl)-5-methylamino-4-methyl-4H-1,2,4-triazol-3-yl-carboxamidate.

14. A compound according to claim 3, wherein $R^4$ represents straight-chain or branched halogenoalkyl having 1 to 6 carbon atoms and 1 to 9 identical or different halogen atoms selected from the group consisting of fluorine and chlorine.

15. A compound according to claim 3, wherein $R^4$ represents straight-chain or branched halogenoalkenyl in each case having 3 to 5 carbon atoms and 1 to 3 halogen atoms selected from the group consisting of fluorine and chlorine.

* * * * *

UNITED STATES PATENT AND TRADEMARK OFFICE
CERTIFICATE OF CORRECTION

PATENT NO. : 5,234,897
DATED : August 10, 1993
INVENTOR(S) : Findeisen, et al.

It is certified that error appears in the above-indentified patent and that said Letters Patent is hereby corrected as shown below:

| | |
|---|---|
| Col. 22, line 50 | After " in " insert -- each of -- |
| Col. 23, line 7 | Delete " or " (third occurrence) |
| Col. 23, lines 13-14 | Delete " dialkyloaminoalkyl " and substitute -- dialkylaminoalkyl -- |
| Col. 23, line 30 | Delete " aryl " (first occurrence) and substitute -- aroyl -- |
| Col. 23, line 67 | Delete " halogenalkinyl " and substitute -- halogenoalkinyl -- |
| Col. 25, line 3 | After " t-bulyl, " delete " cyano " |
| Col. 25, line 5 | Delete " trifluormethylsulphinyl " and substitute -- trifluoromethylsulphinyl -- |
| Col. 25, lines 6-7 | Delete " methylsulphinyl " (second occurrecne) and substitute -- methylsulphonyl -- |
| Col. 25, lines 51-52 | Delete " dialkyloaminoalkyl " and substitute -- dialkylaminoalkyl -- |

UNITED STATES PATENT AND TRADEMARK OFFICE
CERTIFICATE OF CORRECTION

PATENT NO. : 5,234,897
DATED : August 10, 1993
INVENTOR(S) : Findeisen, et al.

It is certified that error appears in the above-indentified patent and that said Letters Patent is hereby corrected as shown below:

| | |
|---|---|
| Col. 25, line 66 | Delete " phehylcyanomethyl, pheylcyanoethyl " and substitute -- phenylcyanomethyl, phenylcyanoethyl -- |
| Col. 26, line 9 | Delete " trifluormethylsulphinyl " and substitute -- trifluoromethylsulphinyl -- |
| Col. 26, lines 10-11 | Delete methylsulphinyl " (second occurrence) and substitute -- methylsulphonyl -- |
| Col. 26, line 42 | Delete " carbooxamidate " and substitute -- carboxamidate -- |
| Col. 28, line 11 | Delete " an " and substitute -- a -- |
| Col. 28, line 24 | Delete " methylylamino " and substitute -- methylamino -- |
| Col. 28, line 26 | After " N- " insert -- ( -- |

Signed and Sealed this

Twenty-third Day of May, 1995

Attest:

BRUCE LEHMAN

*Attesting Officer*    *Commissioner of Patents and Trademarks*